US006183979B1

(12) United States Patent
Lee et al.

(10) Patent No.: US 6,183,979 B1
(45) Date of Patent: Feb. 6, 2001

(54) PREPARATION OF DRIED SYNTHETIC PROTHROMBIN TIME REAGENTS

(75) Inventors: Ted C. K. Lee, Matawan, NJ (US); Paul Michael D'Agostino, Staten Island, NY (US); Anne Jessica Gorman, Jamesburg, NJ (US)

(73) Assignee: International Technidyne Corporation, Edison, NJ (US)

( * ) Notice: Under 35 U.S.C. 154(b), the term of this patent shall be extended for 0 days.

(21) Appl. No.: 09/275,338

(22) Filed: Mar. 24, 1999

(51) Int. Cl.$^7$ ................................. C12Q 1/56; C07F 9/02
(52) U.S. Cl. .................................. 435/13; 554/79
(58) Field of Search ................................ 435/13; 554/79

(56) References Cited

U.S. PATENT DOCUMENTS

| | | | | |
|---|---|---|---|---|
| 4,416,812 | * | 11/1983 | Becker et al. | 260/112 |
| 4,756,884 | * | 7/1988 | Hillman et al. | 422/73 |
| 4,860,829 | * | 8/1989 | Carlberg et al. | 166/279 |
| 4,873,194 | * | 10/1989 | Sawamura et al. | 435/13 |
| 5,110,727 | * | 5/1992 | Oberhardt | 435/13 |
| 5,192,743 | * | 3/1993 | Hsu et al. | 514/8 |
| 5,584,875 | * | 12/1996 | Duhamel et al. | 623/1 |

OTHER PUBLICATIONS

R. Bruce Martin; Introduction To Biophysical Chemistry; Metal Ions in Biological Systems; (1964), p. 337.
Carpenter et al.; The Mechanism of Cryoprotection of Proteins by Solutes; Cryobiology 25, (1988), p. 244–252.
Bach et al.; Purification and Characterization of Bovine Tissue Factor; The Journal of Biological Chemistry, vol. 256, No. 16, (Aug. 25, 1981), p. 8324–8331.
Bach et al.; Factor VII Binding to Tissue Factor in Reconstituted Phospholipid Vesicles: Induction of Cooperativity by Phosphatidylserine; Biochemistry (1986), 25, p. 4007–4020.
Broze, Jr., et al.; Purification of Human Brain Tissue Factor; The Journal of Biological Chemistry; vol. 260, No. 20 (Sep. 15, 1985), p. 10917–10920.
Coots, et al.; A Factor V Inhibitor: In Vitro Interference by Calcium; American Journal of Hematology 7: (1979), p. 173–180.
Properties of Common Amino Acids; CRC Handbook of Chemistry and Physics; (1996) p. 7–1.
Buchner et al.; Thrombosis Et Diathesis Haemorrhagica; vol. 1, (1957), p. 393–395.
Hecht et al.; Thrombosis Et Diathesis Haemorrhagica; vol. XXI, (1969), p. 547–560.
Jawetz, et al.; Review of Medical Microbiology; Chapter 7; (1978); p. 86.
Gregoriadis; Lipid Peroxidation in Liposomes; Liposome Technology; vol. 1, (1984); p. 139–161.
R.R.C. New; Liposomes—A Practical Approach; (1997), p. 17–18.
Pauling; College Chemistry; The Chemistry of the Transition Metals; Chapter 23; (1964), p. 640.
Nemerson; The Phospholipid Requirement of Tissue Factor in Blood Coagulation; The Journal of Clinical Investigation; vol. 47; (1968); p. 72–80.
Powers; Diagnositc Hematology—Clinical and Technical Principles; (1989), p. 482.
Philippot et al.; A Very Mild Method Allowing the Encapsulation of Very High Amounts of Macromolecules Into Very Large (1000 nm) Unilamellar Liposomes; Biochimica et Biophysica Acta, 734 (1983); p. 137–143.
Mimms et al.; Phospholipid Vesicle Formation and Transmembrane Protein Incorporation Using Octyl Glucoside; Biochemistry, 20, (1981) p. 833–840.
Miletich, J.P.; Williams Hematology, Fifth Edition; (1972); p. L82–L84.
Albert L. Lehninger; Biochemistry—The Molecular Basis of Cell Structure and Function, (1970), p. 48–49.
Lawson et al.; Cooperative Activation of Human Factor IX by the Human Extrinsic Pathway of Blood Coagulation; The Journal of Biological Chemistry, vol. 266, No. 17, (Jun. 15, 1991), p. 11317–11327.
Quick, A.J.; Society of Biological Chemists; The Journal of Biological Chemistry, vol. 109, (1935), p. 23–24.
Marsh; CRC Handbook of Lipid Bilayers; (1990), pp. 211–225 and 275–280.
Gregory Gregoriadis; Liposome Preparation and Related Techniquies; Liposome Technology $2^{nd}$ Edition, vol. 1, (1993); p. 234.

* cited by examiner

Primary Examiner—Ardin H. Marschel
Assistant Examiner—Marjorie A. Moran
(74) Attorney, Agent, or Firm—Arthur L. Plevy; Buchanan Ingersoll PC (57) ABSTRACT

A method for preparation of an air-dried prothrombin time (PT) reagent which uses a recombinant protein and synthetic phospholipids is described. The source for the recombinant protein is rabbit brain, and the phospholipids employed are palmitoyloleoylphosphatidylcholine (POPC) and palmitoyloleoylphosphatidylserine (POPS). The particular formulation buffer used to dilute the lipidated tissue factor provides a reagent that is dried without lyophilization and remains stable for at least 2 weeks at 37 C. A method for preparing the improved PT reagent and a method of using the reagent to analyze blood PT is also provided.

19 Claims, 4 Drawing Sheets

PREPARATION OF DRIED SYNTHETIC PROTHROMBIN TIME REAGENTS

BACKGROUND OF THE INVENTION

1. Field of the Invention

The present invention relates to prothrombin time reagents for monitoring extrinsic blood coagulation activities, a method for preparing the reagent and a method for using the reagent. More particularly, the invention relates to a dried synthetic prothrombin time reagent prepared from recombinant tissue factor and synthetic phospholipids, and dried under ambient conditions.

2. Description of Related Art

Blood coagulation tests may be performed for a variety of purposes, including determination of the bleeding susceptibility of patients undergoing surgery and monitoring of patients undergoing anti-coagulation therapy for the prevention of blood clots. A number of coagulation tests presently are in use. One of these tests is the "prothrombin time" (PT) test. The PT test relies upon the induction of the extrinsic coagulation protease factor VIIa by thromboplastin in a blood sample to be tested. The extrinsic coagulation pathway results in the production of thrombin, a proteolytic enzyme that catalyzes the conversion of fibrinogen to fibrin, which is essential to the clotting process.

Thromboplastin, also known as tissue factor, is a membrane associated glycoprotein that forms a complex with blood coagulation factors VIIa. The complex formed enhances the proteolytic activity of these two factors. The functional activity of prothrombin depends on the presence of phospholipids (Bach, Ronald R., Initiation of Coagulation by Tissue Factor, CRC Critical Reviews in Biochemistry 1988; 23(4): pp.339–368). Once formed, the factor VIIa/tissue factor complex activates a series of specific enzymes that comprise the extrinsic and common pathways of the coagulation cascade, which ultimately lead to the formation of thrombin, fibrin, platelet activation, and finally clot formation (Nemerson, Yale, Tissue Factor and Hemostasis, Blood 1988; 71: pp. 1–8).

The prothrombin time (PT) test utilizes this series of enzymatic events in vitro under controlled conditions to diagnose dysfunctions or deficiencies in the blood coagulation system of patients. Other uses include the monitoring of patients undergoing anticoagulant therapy. The time period it takes for clot formation to occur is the Prothrombin Time, or PT value.

PT reagents are used to monitor the coagulation activities of the extrinsic pathway of plasma, including those from patients on Coumadin therapy. For the PT test, a highly sensitive reagent with an International Sensitivity Index (ISI) of 1.0 is desired. With an ISI of 1.0, the calculation of the International Normalized Ratio (INR) of PT coagulation test is simplified.

A PT reagent must have the following characteristics: sensitivity to abnormal samples, a well-defined normal PT value for normal plasma, providing accurate and reproducible results, maintaining consistency from lot to lot, and stability for storage in a dried state and upon reconstitution.

Tissues of vertebrates that have been added to citrated plasma and then recalcified accelerate clotting time. The tissue constituent that activates the coagulation protease cascade is commonly referred to as thromboplastin, or tissue factor (TF). Tissue factors employed in the present PT tests contain crude tissue factor extracted from natural sources. Natural sources include rabbit brain, rabbit brain/lung tissue mixtures, human placenta, or ox brain. Each of these sources has problems associated with them. For example, rabbit brain thromboplastin shows some seasonal variability, it varies from lot to lot, and is in relatively short supply. Human tissue factor may contain HIV or other viral diseases. Ox brain provides values that are much longer than those observed when employing tissue factor from alternative sources. The longer values may reflect differences in the ability of ox tissue factor to bind human factor VII. Crude tissue factor preparations from natural sources also contain other coagulation factors as contaminants. The contamination with coagulation factors results in coagulation factor assay curves that are less sensitive to factor-deficient plasmas.

Tissue factor requires phospholipids for functional activity. Phospholipids found in PT reagents generally are those that adhere to tissue factor when it is extracted from animal sources. For example, the extraction of rabbit brain results in the concurrent isolation of both tissue factor and naturally occurring phospholipids which are bound to the tissue factor in vivo and survive the extraction process. No additional lipids are usually added to such extracted tissue factor. As a result, the nature, quantity, and quality of the lipids employed in the PT reagent will therefore vary depending upon the starting tissues and the extraction process, and will lead to lot to lot inconsistencies. The DADE® thromboplastin reagents, Thromboplastin C, C+, and IS, available from Dade International, Inc. of Deerfield, Ill., are all based on extracts of acetone-dehydrated rabbit brain. Partially purified extracts are blended with specific mixtures of buffers and stabilizers. Since the partially purified tissue factor extract is not completely delipidated, the addition of lipids back into the extract is unnecessary. The nature and composition of the resulting lipids is not well defined and can vary from lot to lot.

Different thromboplastin preparations either improve or reduce discrimination between blood samples having different prothrombin times. Thromboplastins with greater discrimination are termed "more sensitive." The liquid phase sensitivity of a preparation is graded by use of the international sensitivity index. The value is found by plotting on a logarithmic scale, the prothrombin time seen with a thromboplastin lot in question versus the prothrombin time values seen with a standardized lot of thromboplastin. The ISI value is the slope of the resulting line multiplied by the ISI of the reference thromboplastin. More sensitive thromboplastins have lower ISI numbers around 1.0, and less sensitive thromboplastins have higher ISI numbers, typically around 2 to 3.

In attempting to avoid the problems associated with tissue factor from natural sources, the use of recombinant tissue factor for use in a PT reagent is described in U.S. Pat. No. 5,625,036 titled "Preparation of Prothrombin Time Reagents from Recombinant Human Tissue Factor and purified Natural and Synthetic Phospholipids" issued Apr. 29, 1997 to P. L. Hawkins, et al., incorprated herein by reference. As described in the patent, human tissue factor is cloned and expressed in a number of organisms including *E. coli*. A portion of the cloned tissue factor is employed in the PT reagent without loss of functional activity, since most of the intracellular (cytoplasmic) domain of the cloned tissue factor can be truncated. The PT reagent includes recombinant tissue factor, phospholipids, either synthetic or natural, calcium ion, and a buffer composition. Well known cryopreservatives may also be added such as trehalose, maltose, and mannitol. Hawkins and other prior art preparation methods invariably require lyophilization or freeze-drying of the reagent for stability upon storage.

U.S. Pat. No. 5,314,695 titled "Tissue Factor Based Prothrombin Time Reagent" issued May 24, 1994 to S. M. Brown, incorporated herein by reference, relates to a tissue factor prothrombin time reagent in which the tissue factor is inserted into the phospholipid bilayer of liposomes or phospholipid vesicles. A buffer containing a cryopreservative and glycine preferably forms part of the formulation. Either natural tissue factor or recombinant tissue factor can be used. The formulation composition is adjusted to allow maximum coagulant activity and sensitivity to extrinsic coagulation factors. Brown's described preparation methods also require lyophilization.

U.S. Pat. No. 5,358,853 titled "Liquid Thromboplastin Reagent" issued Oct. 25, 1994 to J. R. Butler, et al., included herein by reference, describes a stable liquid thromboplastin reagent with a long shelf life which is prepared without lyophilization. However, the crude rabbit brain extract and unpurified phospholipids which comprise the liquid thromboplastin reagent of U.S. '853 can affect sensitivity variability of the reagent with regard to the PT test.

U.S. Pat. No. 5,418,141 titled "Test Articles for Performing Dry Reagent Prothrombin Time Assays" issued May 23, 1995 to S. E. Zweig, et al., incorporated herein by reference, relates to test articles for performing dry reagent prothrombin time assays. The test articles comprise a solid phase membrane having dry, lyophilized thromboplastin immobilized therein. Coagulation neutral agents that facilitate rehydration of the dry thromboplastin are also provided on the solid phase membrane.

There remains a need therefore for a highly sensitive and consistent PT reagent that also remains stable upon drying without lyophilization or impregnation into a membrane matrix, thereby rendering it easier to manufacture, handle, transport, and store.

SUMMARY OF THE INVENTION

Briefly described, the invention comprises a PT reagent, a method of producing a PT reagent with a high degree of reproducibility for determining PT values, and a method of using the reagent. The inventive reagent is also highly stable upon drying at temperatures above 10° C. in air, nitrogen, or a vacuum. The inventive dried reagent has a long shelf life at 20° C. and remains stable at 37° C. for two weeks or longer.

Recombinant rabbit brain tissue factor is solubilized and mixed with a mixture of synthetic phospholipids in an appropriate ratio. Suitable synthetic phospholipids include palmitoyloleoylphosphatidylcholine and palmitoyloleoylphosphatidylserine. In a preferred embodiment, the phospholipids are solubilized in a suitable detergent such as is octylglucoside dissolved in a suitable buffer such as Hepes buffer,(4-(2-hydroxyethyl)-1-piperazineethanesulfonic acid) containing other ancillary ingredients, such as e.g., a salt such as sodium chloride(NaCl), an antioxidant such as BHT (butylated hydroxytoluene), a carrier protein such as bovine serum albumin, and a humectant such as sorbitol (D-glucitol). Upon solubilizing the components, the solution is subjected to dialysis.

A hydrophobic resin such as polystyrene or polyacrylic resin, and the like, is optionally placed in the dialysis medium to increase dialysis efficiency. The dialysis medium comprises e.g. a buffer such as Hepes buffer, a salt such as sodium chloride, an amino acid chelating agent such as serine (2-amino-3-hydroxyproprionic acid), and a humectant such as sorbitol.

Upon completion of dialysis, the inventive composition is formulated and dried above 10° C. in air, nitrogen or a vacuum in a relative humidity above about 2% RH. Other combinations of temperature, gas composition, and humidity may be used provided that they allow the inventive composition to dry to the final desired moisture level, preferably about 2 to 10% moisture (by weight), in the desired time period. The dried materials are stored in a suitable container and are reconstituted with water for use in coagulation-based assays when needed.

The reconstituted, air-dried reagent of the present invention is suitable for use in coagulation instruments such as the Fibrometer, MLA instrument of Medical Laboratory Automation Inc (Pleasantville, N.Y.), and the ACL instrument of Instrumentation Laboratories, Inc. (Lexington, Mass.).

BRIEF DESCRIPTION OF THE DRAWINGS

The above and other features and aspects of the present invention will become more apparent upon reading the following detailed description in conjunction with the accompanying drawings, in which.

DETAILED DESCRIPTION OF THE INVENTION

Figure 1:
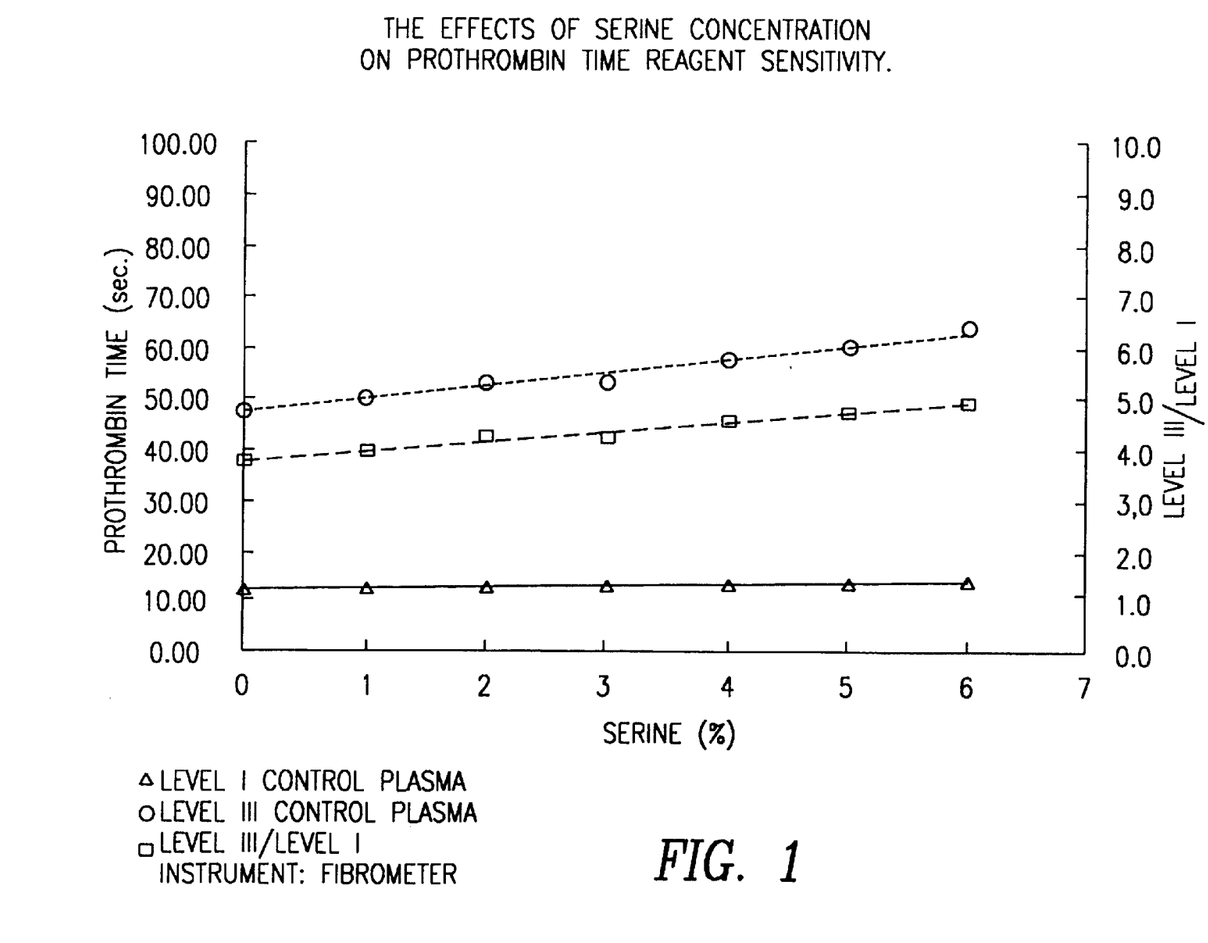
FIG. 1 is a graph showing the effect of serine concentration on the sensitivity of the prothrombin time reagent of the invention. On the "X" axis is shown the concentration of serine. The "Y" axis shows the prothrombin time in seconds, and the relative sensitivity of the assay expressed as a ratio of clotting times of Level III control plasma over Level I control plasma. The control plasmas used were the products of Ortho Diagnostics Corporation (Somerville, N.J.).
Figure 2:
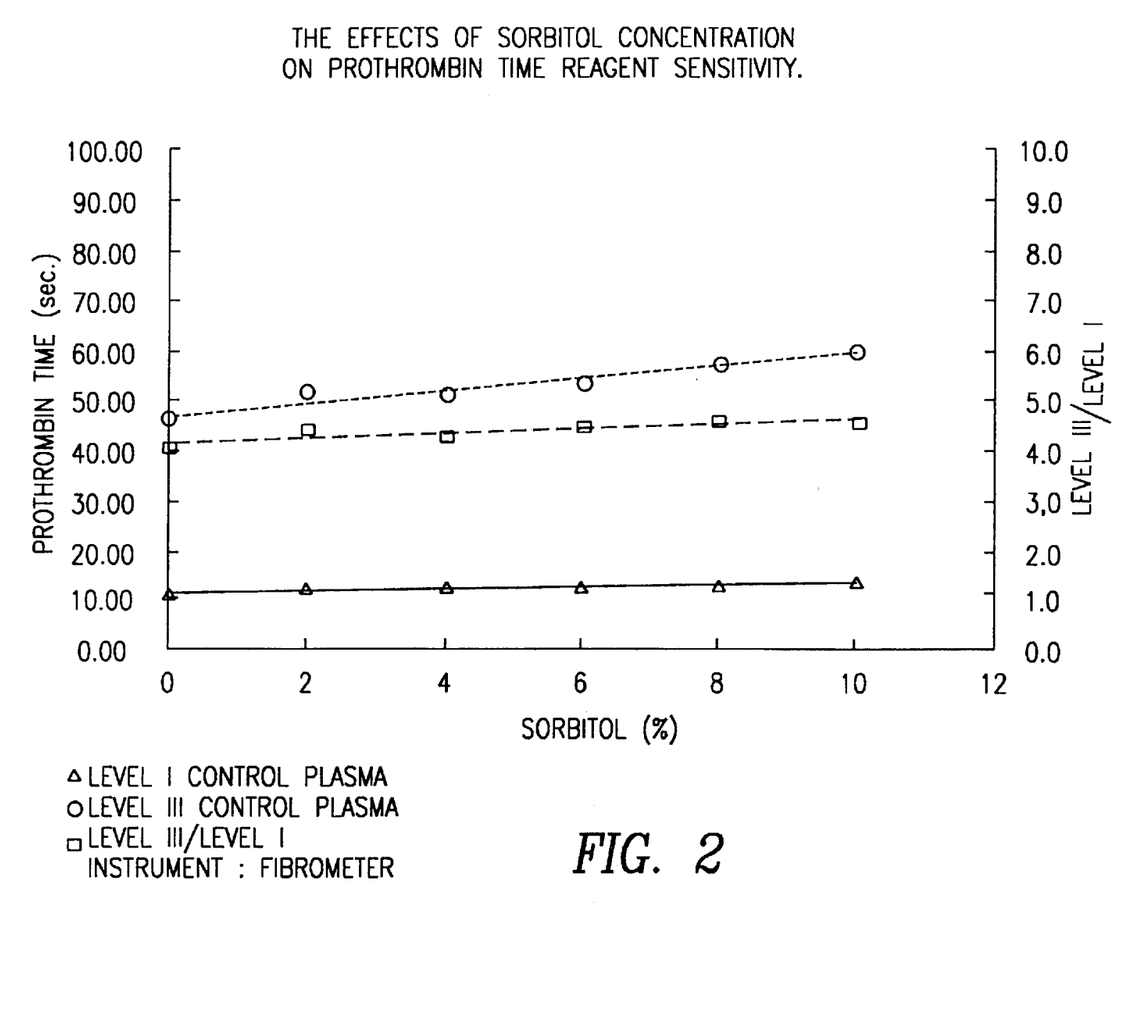
FIG. 2 is a graph showing the effect of sorbitol concentration on the sensitivity of the prothrombin time reagent of the invention. On the "X" axis is shown the concentration of sorbitol. The "Y" axis shows the prothrombin time in seconds, and the relative sensitivity of the assay expressed as a ratio of Level III/I.
Figure 3:
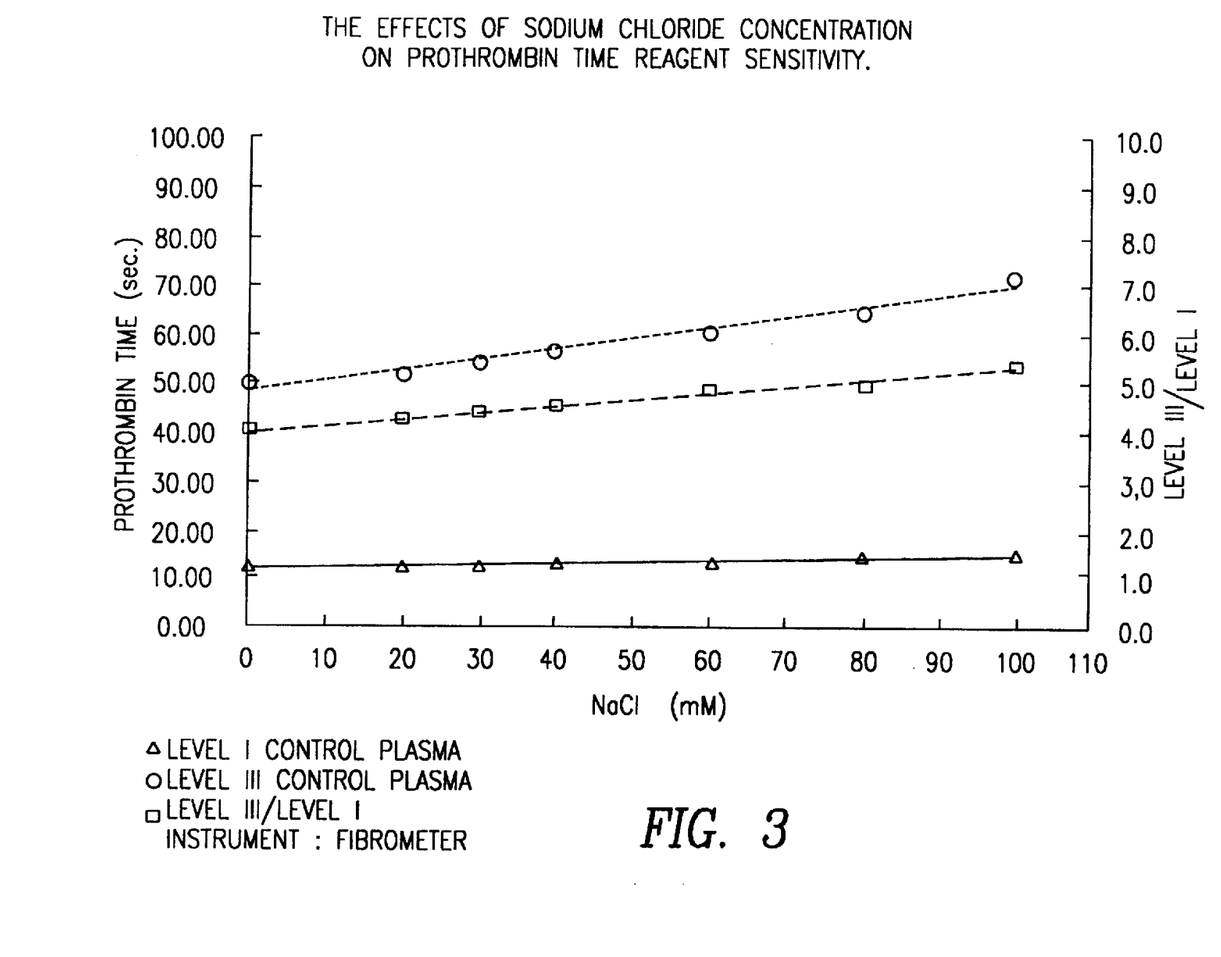
FIG. 3 is a graph showing the effect of sodium chloride concentration on the sensitivity of the prothrombin time reagent of the invention. On the "X" axis is shown the concentration of sodium chloride. The "Y" axis shows the prothrombin time in seconds, and the relative sensitivity of the assay-expressed as a ratio of Level III/I.
Figure 4:
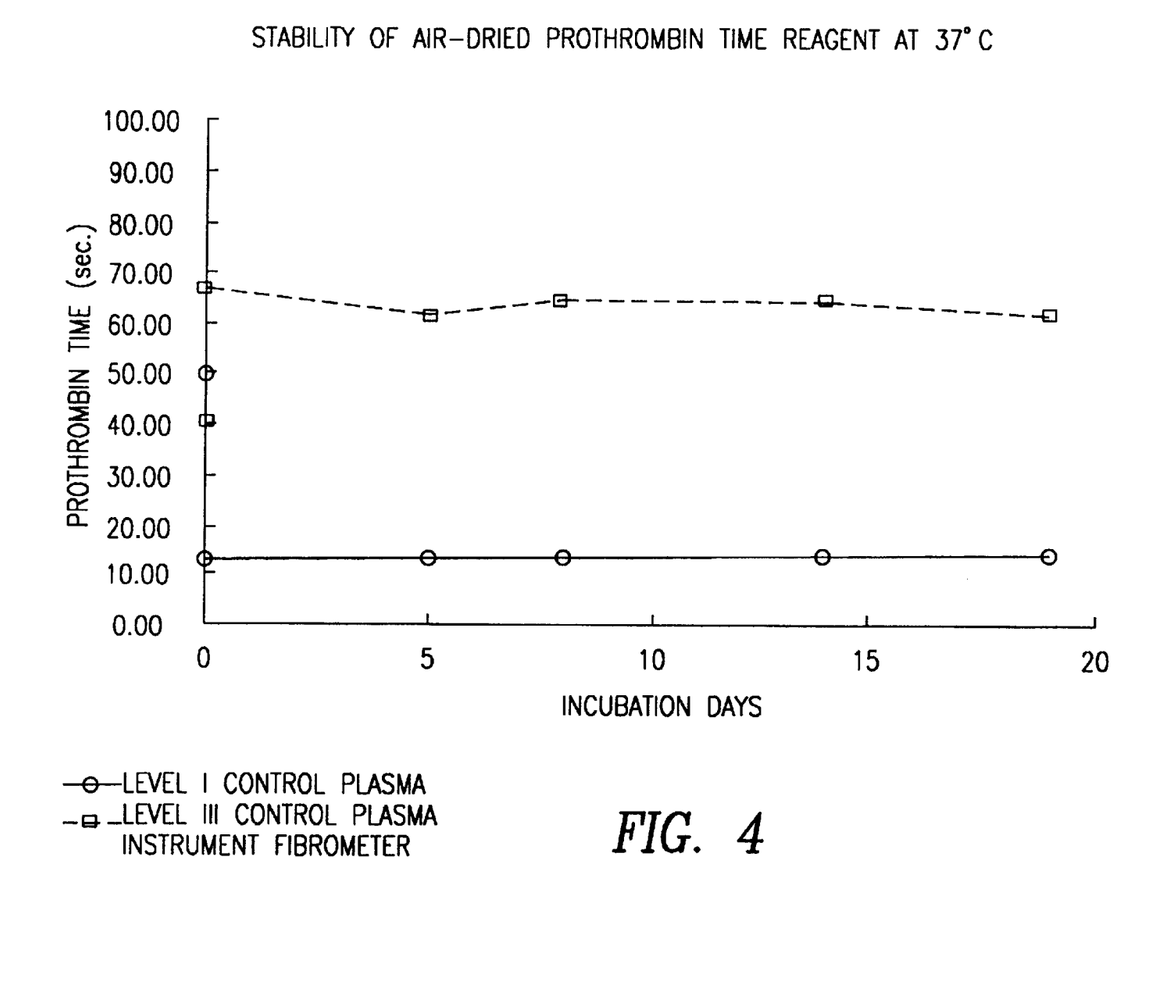
FIG. 4 is a graph showing the stability of air-dried the prothrombin time reagent of the invention at 37° C. On the "X" axis is shown the number of incubation days. The "Y" axis shows the prothrombin time in seconds.

The prothrombin time reagent and methods of the present invention employ animal recombinant protein tissue factor and one or more synthetic phospholipids comprising e.g. palmitoyloleoylphosphatidylcholine (POPC) and palmitoyloleoylphosphatidylserine (POPS) for monitoring the activity of the extrinsic blood coagulation pathway.

In the present invention, the recombinant tissue factor is preferably combined With a mixture of two synthetic phospholipids. Preferably, recombinant tissue factor derived from rabbit brain is employed. Recombinant tissue factor (r-TF) derived front rabbit brain is available from a number of commercial sources. For example, in the present invention, a suitable r-TF derived from rabbit brain is available as a clear solution from Pel Freeze, Inc. of Rogers, Ark.; and is characterized as an apoprotein consisting of a fusion molecule of approx 45 Kd, containing extracellular and transmembrane domains of tissue factor, plus an amino terminal leader sequence consisting of several domains including a bacterial protein thioredoxin which aid in expression and purification. The thioredoxin rTF conjugate has a greater solubility than rTF, which aid in handling of the protein. U.S. Pat. No. 5,858,724 titled "Recombinant Rabbit Tissue Factor", issued Jan. 12, 1999 to R. E. Novy Jr., et al., contains a further description of a suitable r-TF and is here incorporated by reference. The tissue factor is solubilized in a suitable detergent, e.g. octylglucoside and then combined with a mixture of synthetic phospholipids. Preferably, the concentration of the r-TF for the reagent preparation is 200 to 250 μg/ml or greater.

Synthetic phospholipids, which are conveniently obtained from the manufacturer in ampoule form, containing 25 mg each, are mixed together in a suitable ratio for the present composition. The synthetic phospholipids utilized in the present invention may have variations in the fatty acid side chains that are not found in naturally occurring phospholipids. Preferably, the synthetic lipids employed are 1-palmitoyl-2-oleoylphosphatidylcholine (POPC) and 1-palmitoyl-2-olcoyl-phosphatidylserine (POPS), and the like. In a preferred embodiment, POPC and POPS are added in a molar ratio range of about 6:4 to 8:2 respectively. preferably about 7:3. The preferred synthetic lipids have been previously described by J. H. Lawson and K. G. Mann, J.Biol., Chem., 266, 11317 (1991). Synthetic phospholipids provide a more reproducible final product because the functional activity of the reagent is easier to control due to their side chain variations. Another advantage of utilizing synthetic phospholipids as opposed to natural phospholipids is that the composition of natural phospholipids is variable, depending upon the source. In contrast, the chemical composition of synthetic phospholipids is more defined and therefore more consistent.

POPC and POPS are available from a number of commercial sources, including e.g. Avanti Corporation (Alabaster, Ala.), sold under Catalog No. 850457 and 830034, respectively. The synthetic phospholipids are dissolved in a suitable detergent solution such as octylglucoside. Preferably, the phospholipids dissolved in the mixture have a concentration in the range of about 11 to 14 mM preferably in the range of about 12 to 13 mM.

The tissue factor, along with a suitable carrier protein, such as bovine serum albumin (BSA), is lipidated by the dissolved phospholipids by solubilizing in an aqueous solution of a suitable detergent. Octylglucoside (1-O-octyl-D-glucopyranoside) is preferred and is available from Sigma Chemical Co., Catalog No. 08001. Other detergents may be used provided the concentration of micelles or liposomes in the detergent is high enough to permit later dialysis of the solution. The concentration of the detergent e.g. octylglucoside is in the molar ratio of 15 to 65 mM with respect to the phospholipid preferably in the molar ratio of 45 to 50 mM.

Suitable carrier proteins function as a stabilizer for in vitro reactions, especially involving proteins. Suitable carrier proteins include BSA, ovalbumin, and gamma globulin and the like, and are used in a concentration of about 0.01 to 1.0% (by weight). Preferably BSA is used at 0.3% and may be obtained from Sigma Chemical Co. (St. Louis, Mo.).

The inventive solution also optionally contains a suitable antioxidant, especially if air-drying is employed. Antioxidants prevent e.g. the oxidation of lipids to fatty acids. Suitable antioxidants include butylated hydroxytoluene (BHT), butylated hydroxyanisole (BRA), or Vitamin E and the like, in a concentration range of about 0.001 to 0.10% (by weight). Preferably, BHT is used at about 0.01% by weight.

In addition, the solution contains a suitable buffer such as Hepes, MOPS (4-Morpholinepropanesulfonic acid), TES (2-[[tris(hydroxymethyl)methyl]amino]-1-ethanesulfonic acid), DIPSO (3-[bis(2-hydroxyethyl)amino]-2-hydroxy-1-propanesulfonic acid), and the like, in a concentration range of 10 to 100 mM. Preferably the buffer used is Hepes at about 14 mM in concentration.

A salt is used such as sodium chloride, potassium chloride, and the like, in a concentration range of about 0.02 to 0.2 M. Sodium chloride is preferably used in a concentration amount of between about 30 mM and 60 mM.

A suitable amino acid chelating agent is used such as serine, threonine, alanine, and the like, in a concentration range of about 0.1 to 10% (by weight). Amino acid chelating agents can prevent precipitation by chelating contaminants or metal ions that may be present in the composition as a result of the formulation process. Preferably serine is used at about 4 to 5% (by weight).

Suitable amino acids are also employed during micelle or liposome formation during the process of making the inventive composition such as glycine, alanine, serine, and the like. Such amino acids are employed in a concentration of about 1 to 10% (by weight) with respect to the phospholipids. Preferably glycine is used in a concentration of about 4 to 6% (by weight).

One or more humectants are used such as glycerol (1,2,3-propanetriol), glycerol esters, sorbitol, ethylene glycol, propylene glycol, polyethylene glycol, and the like, in a total concentration range of about 1.0 to 10.0% (by weight). Preferably glycerol and sorbitol are used in a concentration range of about 0.1 to 0.5% (by weight) and about 2.0 to 7.0% (by weight), respectively. A humectant, such as sorbitol, is added to the reagent mixture to provide tackiness or stickiness upon air-drying the reagent. Although the mixture can be air-dried to a powder form, it has been found that the tackiness provided by a humectant is preferable when reconstituting the reagent. Moreover, the stickiness prevents the reagent from migrating within a test cuvette. Glycerol, a form of lipid, also imparts stickiness to the reagent, and is also preferably added as a moisture protectant to the solution.

One or more synthetic lipids are dissolved in a suitable detergent solution and recombinant tissue factor is added followed by a carrier protein. The detergent can be removed by several methods known in the art to form a phospholipid tissue factor micelle (see e.g. L. T. Mimms, et al., "Phospholipid Vesicle Formnation and Transmembrane Protein Incorporation Using Octyl Glucoside", Biochemistry, 20, 833–840 (1981), and R. Bach, et al., "Factor VII Bonding to Tissue Factor in Reconstituted Phospholipid Vesicles: Induction of Cooperativity by Phosphatidylserine", Biochemistry, 25, 4007–4020 (1986)). Suitable methods for detergent removal include dialysis, ultrafiltration, hydrophobic chromatography and the like.

In a preferred embodiment, the synthetic phospholipids, POPC and POPS, are dissolved in a detergent solution, in a molar ratio of 7 to 3 respectively and recombinant tissue factor is added. The mixture is incubated at room temperature with gentle shaking for 60 minutes. The detergent in the mixture is then removed by dialysis.

In one preferred method, dialysis proceeds by placing the mixture in a dialysis bag and dialyzing at about 4° C. against one or more Hepes buffer solutions. Dialyzed material in Hepes buffer also preferably contains 5% serine as the amino acid chelating agent 2% sorbitol and 0.1M sodium chloride. In another preferred embodiment, two dialysis solutions are used wherein the first solution contains 5% glycine and the second solution contains 5% serine as the respective amino acid chelating agents. After dialysis, the dialyzed material is drained from the dialysis bag and collected in a sterile polypropylene tube.

The dialyzed mixture containing the lipidated tissue factor is then diluted with a formulation buffer, preferably including Hepes, sodium chloride, serine, sorbitol, BSA, BHT, a suitable biocide, and a suitable calcium ion source.

Suitable ionizable calcium sources include e.g. calcium salts of gluconate, acetate, or chloride and the like in a preferred concentration of range of about 10 to 20 mM. Calcium ions are essential for the activity of calcium dependent coagulation factors, such as Factors II, VII, IX and X. Calcium gluconate is preferred as the calcium ion source, and is preferably added in about a 14 mM concentration.

Suitable biocides include e.g. phenol, and antibiotics such as penicillin or Kanamycin and the like which are added in an effective concentration range to inhibit biogrowth in the inventive composition. Phenol in the concentration range of 0.1 to 0.2% (by weight) is preferred.

The formulated material is dried without lyophilization at a temperature above about 10° C. and a relative humidity of above about 2%. Preferably the material is air-dried at about 20° C. and about 5% relative humidity, to yield a highly stable prothrombin time test reagent. Upon reconstitution with water, the reagent is subjected to coagulation assays employing a traditional prothrombin time test method, using a Fibrometer.

Concerning the International Sensitivity Index (ISI), the inventive reagent provides a value of 1.0±0.05 which greatly simplifies the calculation of the International Normalized Ratio (INR), as is apparent from the following formula for calculating the INR:

$$INR = (PT\ Ratio)^{ISI}$$

The dried product of the present invention has an ISI value of substantially 1.0. An ISI value of 1.0 is preferred, since values reaching 2 or 3 indicate a less sensitive reagent.

The inventive reagent can be placed in a various coagulation instruments for testing. For example, the air-dried reagent is reconstituted and placed in a cuvette of the MLA instrument for assay purposes.

Thus, the highly sensitive reagent is optimized for drying, preferably air-drying under ambient conditions. Rehydration of the reagent is rapid, and the stickiness of the reagent prevents the reagent from moving within the chosen test device prior to reconstitution. The reagent is highly stable. The air-dried reagent, maintained at a temperature of 37° C., remains stable for at least about 2 weeks.

While the invention has been described with reference to the preferred embodiments thereof, it will be appreciated by those of ordinary skill in the art that modifications can be made to the parts that comprise the invention without departing from the spirit and scope thereof. The following examples will serve to further typify the nature of the invention but should not be construed as a limitation on the scope thereof, which is defined solely by the appended claims.

EXAMPLE 1

A highly stable reagent was prepared using the following components: Synthetic phospholipids, palmitoyloleoylphosphatidylcholine (POPC) and palmitoyloleoylphosphatidylserine (POPS) were dissolved at 45° C., respectively, in 600 mM octylglucoside (a detergent), 0.1 mg per ml butylated hydroxytoluene (BHT), 14 mM Hepes, 0.1 M sodium chloride, 5% glycine, and 2% sorbitol, at a pH of 7.4. The concentration of the dissolved phospholipids was 12.76 mM. The dissolved phospholipids were mixed with a molar ratio of 7 to 3 (POPC:POPS) as described in the published procedure by R. Bach, R. Gentry, and Y. Nemerson (Biochemistry, 25, 4007–4020, (1986). Bovine serum albumin (BSA) and recombinant rabbit brain tissue factor were added to make a concentration of 0.06 mg/ml and 40 ug/ml, respectively. The mixture was incubated at room temperature for one hour with gentle shaking to form a homogenous mixture of lipid and tissue factor. Bovine serum albumin was added to make a concentration of 4.8 mg/ml. The mixture was then placed in a dialysis bag, and dialyzed at 4° C. as follows: First the mixture was dialyzed for 48 hours, with agitation, against a first Hepes buffer solution at pH 7.4 containing 14 mM Hepes. 5% (by weight) glycine, 0.1 M sodium chloride, and 2% (by weight) sorbitol. Next the mixture was dialyzed for an additional 24 hours with agitation against a second Hepes buffer solution which was identical to the first solution except that serine was substituted for glycine. The buffer solution dialysis medium was changed 3 to 4 times in each 24 hour period. The mixture was then allowed to remain in the dialysis tube without agitation for an additional 48 to 72 hours after which time the resultant lipidated tissue factor was drained from the dialysis bag. The lipidated tissue factor was diluted 100-fold with a formulation buffer, which was composed of 14 mM hepes, 60 mM sodium chloride, 4.5% serine, 7% sorbitol, 14 mM calcium gluconate, 0.3% BSA, 0.2% phenol and 0.01% BHT, at pH 7.4. The formulated material was air-dried at 20° C. and 5% relative humidity. The air-dried materials were reconstituted with water and subjected to coagulation assay by the traditional prothrombin time test method. /Query The control plasma samples used for the assay were Level I and Level III of Ortho Diagnostics Corporation.

Tables 1–10 show the ratio of a normal control (Level I) to that of an abnormal control (Level III) for plasmas that have been pooled. Level I pooled plasmas are lyophilized with a stabilizer to determine normal factors present in plasma. The resulting Level I serves as a control to mimic the normal factors. Level III plasma control contains a reduced amount of coagulation factors. A coagulation ratio (III/I) of about 4.0 or 5.0 leads to an ISI value of 1. An ISI value of 1 indicates a reagent with high sensitivity. Ratios of 2 or 1 lead to ISI values of 2 or 3, indicating a reagent with reduced sensitivity. Thus, a high (III/I) ratio indicates a reagent with increased sensitivity. As shown in the datum reproduced below in Tables 1–10, the reagent of the present invention has a high degree of sensitivity after the reagent is dried. In a preferred embodiment, the concentration of serine, sorbitol, and sodium chloride is adjusted to obtain the level III/I clotting time ratio of 4.0 to 5.0 (see Examples 1 to 5, and 10).

TABLE 1

| | Clotting Times (Seconds) | | |
|---|---|---|---|
| Reagents | Level I | Level III | III/I Ratio |
| Formulated | 13.4 | 59.4 | 4.43 |
| Air-dried | 12.7 | 56.5 | 4.45 |

EXAMPLE 2

The lipidated tissue factor was diluted 100-fold with a formulation buffer, which is composed of 14 mM Hepes, 30 mM sodium chloride, 4.5% serine, 7% sorbitol, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 2

| Reagents | Clotting Times (Seconds) | | |
|---|---|---|---|
| | Level I | Level III | III/I Ratio |
| Formulated | 13.1 | 56.7 | 4.33 |
| Air-dried | 12.4 | 55.2 | 4.45 |

EXAMPLE 3

The lipidated tissue factor was diluted 100-fold with a formulation buffer, which is composed of 14 mM Hepes, 4.5% serine, 7% sorbitol, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 3

| Reagents | Clotting Times (Seconds) | | |
|---|---|---|---|
| | Level I | Level III | III/I Ratio |
| Formulated | 13.4 | 52.2 | 3.90 |
| Air-dried | 13.4 | 58.9 | 4.40 |

EXAMPLE 4

The lipidated tissue factor was diluted 100-fold with a formulation buffer, which is composed of 14 mM Hepes, 80 mM sodium chloride, 4.5% serine, 7% sorbitol, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 4

| Reagents | Clotting Times (Seconds) | | |
|---|---|---|---|
| | Level I | Level III | III/I Ratio |
| Formulated | 13.4 | 63.2 | 4.72 |
| Air-dried | 12.6 | 58.4 | 4.64 |

EXAMPLE 5

The lipidated tissue factor was diluted 100-fold with a formulation buffer, which is composed of 14 mM Hepes, 100 mM sodium chloride, 4.5% serine, 7% sorbitol, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 5

| Reagents | Clotting Times (Seconds) | | |
|---|---|---|---|
| | Level I | Level III | III/I Ratio |
| Formulated | 13.9 | 65.7 | 4.73 |
| Air-dried | 13.1 | 63.2 | 4.82 |

EXAMPLE 6

The lipidated tissue factor was diluted 100-fold with a formulation buffer, which is composed of 14 mM Hepes, 30 mM sodium chloride, 8% sorbitol, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 6

| Reagents | Clotting Times (Seconds) | | |
|---|---|---|---|
| | Level I | Level III | III/I Ratio |
| Formulated | 13.6 | 48.7 | 3.58 |
| Air-dried | 11.9 | 40.0 | 3.36 |

EXAMPLE 7

The lipidated tissue factor was diluted 100-fold with a formulation buffer, which is composed of 14 mM Hepes, 30 mM sodium chloride, 1.0% serine, 8% sorbitol, 14 mM calcium gluconate, 0.3% BSA, 0.2% phenol, 0.25% glycerol, and 0.01% BHT, pH 7.4. The formulated material was air-dried at 20° C. and 5% relative humidity. The air-dried material was reconstituted with water and subjected to coagulation assay by traditional prothrombin time test method.

TABLE 7

| Reagents | Clotting Times (Seconds) | | |
|---|---|---|---|
| | Level I | Level III | III/I Ratio |
| Formulated | 13.4 | 49.7 | 3.71 |
| Air-dried | 11.85 | 40.9 | 3.53 |

EXAMPLE 8

The lipidated tissue factor was diluted 100-fold with a formulation buffer, which is composed of 14 mM Hepes, 30 mM sodium chloride, 6.0% serine, 8% sorbitol, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 8

| Reagents | Clotting Times (Seconds) | | |
|---|---|---|---|
| | Level I | Level III | III/I Ratio |
| Formulated | 13.9 | 60.2 | 4.33 |
| Air-dried | 13.1 | 66.9 | 5.10 |

EXAMPLE 9

The lipidated tissue factor was diluted 100-fold with a formulation buffer, which is composed of 14 mM Hepes, 30 mM sodium chloride, 4.5% serine, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 9

| Reagents | Clotting Times (Seconds) | | |
|---|---|---|---|
| | Level I | Level III | III/I Ratio |
| Formulated | 12.4 | 49.4 | 3.98 |
| Air-dried | 13.1 | 39.0 | 2.98 |

EXAMPLE 10

The lipidated tissue factor was diluted 100-fold with a formulation buffer, which is composed of 14 mM Hepes, 30 mM sodium chloride, 4.5% serine, 10 sorbitol, 14 mM calcium gluconate, 0.3% BSA, 0.2% phenol, 0.25% glycerol, and 0.01% BHT. The formulated material was air-dried at 20° C. and 5% relative humidity. The air-dried material was reconstituted with water and subjected to coagulation assay by traditional prothrombin time test method.

TABLE 10

| Reagents | Clotting Times (Seconds) | | |
|---|---|---|---|
| | Level I | Level III | III/I Ratio |
| Formulated | 14.4 | 57.9 | 4.02 |
| Air-dried | 13.9 | 63.9 | 4.60 |

What is claimed is:

1. A method for preparing a non-lyophilized air dried prothrombin time reagent used for determining prothrombin time, the method comprising the steps of:
   combining a recombinant fusion protein of bacterial thioredoxin and rabbit brain tissue factor with a mixture of synthetic phospholipids in an amount sufficient to activate said protein; and
   air-drying said protein and mixture combination at a temperature above about 10° C. thereby forming the reagent;
   wherein the air dried reagent remains stable for at least 2 weeks at 37° C.

2. The method of claim 1, wherein the bacterial thioredoxin comprises sequences obtained from *Escherichia coli*.

3. The method of claim 1, wherein the mixture of synthetic phospholipids comprises palmitoyloleoylphosphatidylcholine and palmitoyloleoylphosphatidylserine.

4. The method of claim 1, wherein the mixture includes a HEPES buffer solution having a pH in the range of about 7.0 to about 7.8.

5. The method of claim 1, wherein the mixture includes a calcium compound which provides a source of calcium ions for calcium dependent coagulation factors.

6. The method of claim 1, wherein the reagent has an International Sensitivity Index of substantially 1.0.

7. The method of claim 1, wherein the mixture includes an amino acid chelating agent, a carrier protein, a humectant, and a biocide.

8. The method of claim 7, wherein the amino acid chelating agent includes serine, the carrier protein includes BSA, the humectant includes sorbitol and glycerol, and the biocide includes phenol.

9. The method of claim 5, wherein the calcium ions source is calcium gluconate.

10. A method of preparing a non-lyophilized air dried reagent which is used for determining prothrombin time, the method comprising the steps of:
    adding synthetic phospholipids consisting of palmitoyloleoyl-phosphatidylcholine and palmitoyloleoylphosphatidylserine in a molar ratio range of 6:4 to 8:2 respectively to a solution containing an antioxidant, a buffer, a salt, an amino acid chelating agent, a detergent, and a humectant;
    adding a recombinant fusion protein of bacterial thioredoxin and recombinant rabbit brain tissue factor to said phospholipid solution;
    incubating said protein solution for a selected time at a selected temperature to form a homogeneous mixture;
    dialyzing the mixture of lipid and tissue factor in a selected dialysis medium to remove said detergent and to form lipid vesicles having said tissue factor inserted therein;
    diluting the lipidated tissue factor with a formulation buffer;
    air-drying the formulated lipidated tissue factor at a temperature above about 10° C. and at a selected relative humidity, wherein the air dried reagent remains stable for at least two weeks at 37° C.

11. The method of claim 10, wherein said formulation buffer comprises a buffer, a salt, an amino acid chelating agent, a humectant, a calcium compound, a carrier protein, a biocide, and an antioxidant, and wherein the formulation buffer has a pH in the range of 7.0 to 7.8.

12. The method of claim 10, wherein said selected dialysis medium comprises a first buffer solution containing glycine and a second buffer solution containing serine.

13. The method of claim 10, wherein said reagent has an International Sensitivity Index of substantially 1.0.

14. The method of claim 10, wherein said palmitoyloleoylphosphatidylcholine and palmitoyloleoylphosphatidylserine are blended in a molar ratio range of about 7 to about 3 respectively.

15. The method of claim 10, wherein the antioxidant includes butylated hydroxytoluene, the buffer includes Hepes, the isotonic reagent includes sodium chloride, the amino acid chelating agent includes serine, and the humectant includes sorbitol and glycerol; and the carrier protein includes bovine serum albumin.

16. The method of claim 10 wherein the dialyzed mixture of lipid and tissue factor is incubated at ambient temperature for a selected time.

17. The method of claim 10 wherein the detergent includes octyl glucoside.

18. The method of claim 10 wherein a hydrophobic resin is placed in the dialysis medium.

19. The method of claim 10 where the solution is dried in air in the temperature range of about 10 to about 50° C. and a relative humidity range of about 2 to about 10% R.H.

* * * * *

UNITED STATES PATENT AND TRADEMARK OFFICE
CERTIFICATE OF CORRECTION

PATENT NO. : 6,183,979 B1
DATED : February 6, 2001
INVENTOR(S) : Lee, Ted C.K., D'Agostino, Paul Michael Gorman, Anne Jessica It is certified that error appears in the above-identified patent and that said Letters Patent is hereby corrected as shown below:

<u>Title page,</u>
Section [73], one of the Assignees was omitted. That Section should read:

Assignee: International Technidyne Corporation, Edison, NJ (US) and CareSide, Inc., Culver City, CA (US)

Signed and Sealed this

Thirtieth Day of October, 2001

Attest:

NICHOLAS P. GODICI
*Attesting Officer*   *Acting Director of the United States Patent and Trademark Office*